(12) United States Patent
Nilsson et al.

(10) Patent No.: US 6,909,091 B2
(45) Date of Patent: Jun. 21, 2005

(54) SEPARATION AND ANALYSIS OF SAMPLE COMPONENTS

(75) Inventors: Staffan Nilsson, Lund (SE); Peter Spégel, Helsingborg (SE); Peter Viberg, Lund (SE); Leif Schweitz, Göteborg (SE)

(73) Assignee: Nanosep AB, Stockholm (SE)

( * ) Notice: Subject to any disclaimer, the term of this patent is extended or adjusted under 35 U.S.C. 154(b) by 0 days.

(21) Appl. No.: 10/448,064

(22) Filed: May 30, 2003

(65) Prior Publication Data

US 2004/0238736 A1 Dec. 2, 2004

(51) Int. Cl.⁷ .............................................. H01J 49/04
(52) U.S. Cl. .................... 250/288; 210/198.2; 210/296
(58) Field of Search ...................... 250/288; 210/198.2, 210/296

(56) References Cited

U.S. PATENT DOCUMENTS

6,027,890 A * 2/2000 Ness et al. ..................... 435/6

FOREIGN PATENT DOCUMENTS

WO WO 93/20435 10/1993

OTHER PUBLICATIONS

Hjerten; "Free Zone Electrophoresis"; Institute of Biochemistry, University of Uppsala, Sweden, pp. 122–219, (1967).
Monning et al.; "Capillary Electrophoresis."; Analytical Chemistry, vol. 66, No. 12, pp. 280–314, (1994).
Terabe et al.; "Electrokinetic Chromatography With Micellar Solution and Open–Tubular Capillary"; Analytical Chemistry, vol. 57, No. 4, pp. 834–841, (1985).
Mazzeo; "Micellar Electrokinetic Chromatography"; Handbook of Capillary Electrophoresis, Chapter 2, pp. 49–73, (1997).
Knox et al.; "Miniaturisation in Pressure and Electroendosmotically Driven Liquid Chromatography: Some Theoretical Considerations"; Chromatographia, vol. 24, pp. 135–143, (1987).

(Continued)

Primary Examiner—Jack I. Berman
(74) Attorney, Agent, or Firm—Finnegan, Henderson, Farabow, Garrett & Dunner, LLP

(57) ABSTRACT

The invention describes a new integrated separation and analysis system for analysis and separation of at least one sample component, comprising a mass sensitive detector (1) with ionization source (2), at least one mobile solid phase (3), at least one sample component (4), one transport system (5) where the mobile solid phase and the sample component are transported, and at least one transport fluid (6). The sample component is separated at the interface between the transport and the mass sensitive detector. Also, a method for analysis and separation of sample components is included, utilizing the mentioned integrated separation and analysis system. According to the method, the mobile solid phase and the sample are separated before the mass analyzer, and the sample components are transported towards the mass analyzer.

34 Claims, 12 Drawing Sheets

OTHER PUBLICATIONS

Knox et al.; "Electrochromatography in Packed Tubes Using 1.5 to 50 μm Silica Gels and Ods Bonded Silica Gels"; Chromatograpia, vol. 32, No. 7/8, pp. 317–328, (1991).

Valtcheva et al.; "Chiral Separation of β–Blockers by High=– Performance Capillary Electrophoresis Based on Non–Immobilized Cellulase as Enantioselective Protein"; Journal of Chromatography, vol. 638, pp. 263–267, (1993).

Amini et al.; "Principle and Applications of the Partial Filling Technique in Capillary Electrophoresis"; Chromatographia, vol. 50, No. 7/8, pp. 497–506, (1999).

Schweitz et al.; "Molecularly Imprinted Microparticles for Capillary Electrochromatographic Enantiomer Separation of Propranolol"; Analyst, vol. 125, pp. 1899–1901, (2000).

Dole et al.; "Molecular Beams of Macroions"; The Journal of Chemical Physics, vol. 49, No. 5, pp. 2240–2249, (1968).

Thomson et al.; "Field Induced Ion Evaporation From Liquid Surfaces at Atmospheric Pressure"; J. Chem. Phys. vol. 71, No. 11, pp. 4451–4463, (1979).

Yamashita et al.; "Electrospray Ion Source. Another Variation on the Free–Jet Theme"; The Journal of Physical Chemistry, vol. 88, No. 20, pp. 4451–4459, (1984).

Santesson et al.; "Airborne Cell Analysis"; Analytical Chemistry, vol. 72, No. 15, pp. 3412–3418, (2000).

Chen et al.; "Macroporous Photopolymer Frits for Capillary Electrochromatography"; Analytical Chemistry, vol. 72, No. 6, pp. 1224–1227, (2000).

Behnke et al.; "Fluorescence Imaging of Frit Effects in Capillary Separations"; Electrophoresis, vol. 21, pp. 3102–3108, (2000).

* cited by examiner

Mobile solid phase

Sample

Levitated drop

SEPARATION AND ANALYSIS OF SAMPLE COMPONENTS

TECHNICAL FIELD

This invention relates to separation and analysis of sample components aided by an integrated separation and analysis system comprising at least one mobile solid phase. Furthermore, a method for separation and analysis of sample components using the present system, as well as the use of the system is disclosed.

BACKGROUND OF THE INVENTION

An analytical system usually comprises a separation system and an analysis system. The separation system and an analysis system are usually separated in time and space. A frequently encountered problem is that there is a loss of sample components in one of the systems or in the interface in between the systems.

Most of the analytical methods currently in use in chemical analysis are not completely selective. Because of this, there is a need for separation of the sample components prior to their presentation for the analytical system. At present date the most frequently used separation systems are based on chromatography. The first separation utilizing chromatography was reported by Tswett in 1903[1]. When allowing a plant extract to flow through a column packed with calcium carbonate, the plant pigments where separated in colored bands. The appearance of these colored bands founded the name for the technique, i.e. chromatography (from Greek chromos=color, and grafe=to write). There are some features that are in common for all types of chromatography. A sample is diluted, and transported, in a mobile phase, which can be a liquid, a gas or a supercritical fluid. The mobile phase passes a stationary phase that is immiscible with the mobile phase. The stationary phase is either fixed in a column or bond to a surface. These two phases, i.e. the mobile and the stationary phase, are chosen in a way that allows the sample components to be distributed between them. Different types of sample components will distribute themselves somewhat differently between the phases. Sample components primarily present in the mobile phase will quickly follow this phase through the column. Other components that are staying in the stationary phase for a longer time will also stay a longer time in the column. This difference between different sample components yields a mobility difference, allowing the sample components to be separated from each other. Different types of chromatographic systems arise as a consequence of the different types of mobile and stationary phases that are possible to use.

[1]Tswett, M. S.; Protok, T.; Varshav Obsch. Estestvoispyt Otd. Biol. 14 (1905).

Liquid chromatography (LC) is characterized by a liquid mobile phase. The stationary phase can be either a liquid adsorbed to a solid material, organic molecules bond to solid surface, a solid material, an ion-exchange material or a solid material with interconnected pores. In the porous packing material the sample components are distributed according to their sizes. One advantage with this type of chromatography is that it is compatible with most types of analytical systems that do not destroy the analytes. Furthermore, the LC type of chromatography can be open and handle large quantities of sample for preparative applications.

Gas chromatography (GC) is characterized by a gaseous mobile phase. The stationary phase can be a liquid that is adsorbed to a surface, organic molecules bond to a surface or a solid material. One drawback of this system is that the analytical system used mostly destroys the sample components. An analytical system frequently used in combination with GC is flame ionization detection (FID). Non-volatile compounds can not be analysed with this system and the system must also be closed.

Supercritical fluid chromatography (SFC) is a hybrid of LC and GC. A supercritical fluid has physical properties in-between those of a gas and a liquid. Sample components that are not volatile and does not have chemical groups that enables them to be detected by analytical systems compatible with LC (mass spectrometry excluded) comprises the major part of SFC analyses. A solid material with organic molecules bond to it is most frequently applied as stationary phase.

Capillary electrophoresis (CE) originates from electrophoresis that was developed by Tiselius in 1937 for analysis of bio-macromolecules[2]. The basis of electrophoresis is the mobility of a charged component in a solution over which an electric field has been applied. The mobility of the component is related to its charge state and its friction against the surrounding media. The frictional force is related to the size of the compound, i.e. the hydrodynamic radius. A current evolves as charged species starts to migrate in an electric field and thus heat is emitted. In order to reduce the magnitude of the generated heat, CE was invented[3,4] to allow efficient heat emission from the separation media. A flat flow velocity profile is obtained in CE due to the formation of an electrical double layer at the inner walls of the capillary. This flat flow velocity profile allow the analytes to be forced unselectively through the capillary with a velocity independent of where in the cross-section of the capillary the analyte is situated. The obtained separation efficiency is therefore considerably higher than that obtained in LC, and then especially for bio-macromolecules which have very low diffusion coefficients[5].

[2]Tiselius, A. Trans. Faraday Soc. 1937, 33, 524.
[3]Hjertén, S., Chromatogr. Rev. 1967, 9, 122.
[4]Virtanen, R. Acta Polytechnica Scand. 1974, 123, 1.
[5]Monnig, C. A. and Kennedy, R. T. Anal. Chem. 1994, 66, 280R.

Micellar electro kinetic chromatography (MEKC) utilizes the distribution of sample components between the mobile phase (electrolyte) and micelles in the electrolyte[6]. The system is useful for separation of sample components with the same electrophoretic mobility but with different affinities for the micelles. MEKC has primarily been applied to separations of neutral sample components, sample components having the same mass to charge ratio and chiral sample components[7].

[6]Terabe, S. T., Otsuka, K., and Ando, T., Anal. Chem. 1985, 57, 834.
[7]Mazzeo, J. R., Micellar electrokinetic chromatography, Handbook of Capillary Electrophoresis 2nd ed. 1997, CRC Press, Inc.

Capillary electrochromatography (CEC) is a hybrid between CE and LC. A major difference between CE and LC is that the sample is transported through the separation system in a flat flow velocity profile, compared to the parabolic flow velocity profile found in LC. The separation mechanism is a combination of the electrophoretic mobilities of the sample components and the different distributions of the sample components between the electrolyte and the stationary phase. The stationary phase can either be particle based, packed inside the capillary, or monolithic, i.e. a continuous stationary phase with interconnected pores. It has been shown both theoretically[8] and experimentally[9] that the separation efficiency in CEC is superior to that in LC.

[8]Knox, J. H. and Grant, I. H., Chromatographia 1987, 24, 135, 1987.
[9], J. H. and Grant, I. H., Chromatographia 1991, 32, 317.

Separations have also been performed utilizing a mobile solid phase in a partial filling application[10,11] of CEC (FIG. 1.). Molecularly imprinted polymer (MIP) nanoparticles have been used to perform highly efficient enantiomer separations of chiral sample components utilizing partial filling CEC with UV-detection[12]. The primary benefit of the partial filling technique is that a mobile solid phase can be used without hampering the analysis system. The mobile solid phase is suspended in the electrolyte and injected as a plug with a certain length prior to the sample. The separation system is designed (length of plug and length of capillary) so that the sample has time to migrate through the particle plug and reach the detection window prior to the light scattering and light absorbing particle plug. The drawbacks of the partial filling technique are related to the difficulties associated with the adjustment of the migration velocities of the sample components and the mobile solid phase particle plug. The system must be designed to enable the sample components to pass the particle plug and reach the detection window prior to the particle plug.

[10]L. Valtcheva, J. Mohammad, G. Pettersson, S. Hjertén *J. Chromatogr.* 1993, 638, 263–267.
[11]A. Amini, U. Paulsen-Sorman, D. Westerlund, *Chromatographia* 1999, 36, 35.
[12]Schweitz, L., Spégel P., Nilsson, S. *Analyst* 2000, 125, 1899–1901.

In common for all above mentioned separation systems is that the solid phase (i.e. the stationary phase or the mobile solid phase) is not directly compatible with the analysis system. The separation system thus suffers from irreversible adsorption of sample components onto the solid phase that will never reach the analysis system. These sample components will thus never be detected and determined. The analysis system is most often situated at the outlet of the separation system, imaging detection devices excluded[13].

[13]Method and detection for separation processes, PCT/SE93/00305

Mass spectrometers (MSs) are analysis systems that analyzes charged (ionic) sample components. The creation of gaseous ions from charged droplets is referred to as electro spray ionization (ESI). ESI was suggested as an ionization source for MS in the early 1960's by Dole et al.[14] Today ESI is one of the most common ionization sources for MS. Dole proposed a mechanism for ESI that was called the charged residual model (CRM). CRM (FIG. 2.) describes the fast size reduction of a small (nanometer to micrometer) charged droplet accelerated in an electric field. The size reduction is due to solvent evaporation, which proceeds until the Rayleigh limit of the droplet is reached, i.e. the limit where the repulsive forces between charges on the surface of the droplet are larger than the surface tension keeping the droplet together. As this limit is passed the droplet explodes, causing the formation of several smaller droplets. In the end, following several repetitions of evaporations and explosions, respectively, a single droplet only contains one or two sample components. Charges present in the droplet will be transferred to the sample components during CRM. In 1979 Irbane et al presented a similar model for the creation of gaseous ions[15].

[14]Dole, M.; Mach, L. L.; Hines, R. L.; Mobley, R. C.; Ferguson, L. P.; Alice, M. B. *J. Chem. Phys.* 1968, 49, 2240.
[15]Thomson, B. A.; Irbane, J. V. *J. Chem. Phys.* 1979, 71, 4451.

In the middle of the 1980's, Fenn et al demonstrated a functional ES-MS[16]. The combination of ESI and MS requires that charged droplets can be created from the sample component solution. This can be achieved by allowing the sample to be pumped through a flow column, most often a capillary, while applying a potential difference (voltage) between the capillary outlet end and the inlet to the MS. In positive mode operation a voltage in the kilo volt range is usually applied to the capillary outlet while the inlet to the MS is grounded. In negative mode operation the capillary outlet will be grounded and a voltage in the kilo volt range will be applied to the inlet of the MS. When operating the MS in positive mode, positively charged ions are drawn from the capillary towards the inlet of the MS. The positively charged ions will withdraw solvent and sample components present in the solvent. Following CRM, single charged sample ions are finally generated. In the negative mode, negative ions are attracted by the inlet of the MS.

[16]Yamashita, M.; Fenn, J. B. *J. Chem. Phys.* 1984, 88, 4451.

One disadvantage when considering coupling of a separation system with an ESI-MS is that the same separation column is used for long periods of time due to the costs of purchasing these columns. This is especially true for packed capillary columns. MEKC comprises a different type of chromatography where a new selector phase is used in every new separation. However, MEKC can not be used directly with an MS since the micelles and surfactants present in the mobile phase will contaminate the MS, increase the noise and lower the ionization efficiency of the sample components leading to detection limit reductions.

Absorption of sample components to the sample handling equipment is a major problem in analytical chemistry. This problem needs to be particularly addressed today as the evolution of the analytical chemistry is directed towards miniaturization, e.g. analysis of a single living cell. According to the discussion above it is of great concern to develop and invent systems and methods that are able to handle, separate and analyze samples in an efficient manner without loss of sample components. The invention described in this application offers a unique solution to these problems.

SUMMARY OF THE INVENTION

Having the above described problems in mind, e.g. well known problems in separation and analysis applications relating to adsorbtion of sample components to handling equipment, this invention provides a new and improved system for separation and analysis of sample components.

The goal of the described invention is to provide an efficient system for separation and analysis of sample components, as well as a method for efficient separation and analysis of sample components enabling exclusion of the above discussed problems.

An integrated separation and analysis system is accordingly disclosed for analysis and separation of at least one sample component. The system comprises a mass sensitive detector (1) with an ionization source (2), at least one mobile solid phase (3), at least one sample component (4), a transport system (5) in which the mobile solid phase and the sample components are carried, and at least one transport fluid (6). The sample components are separated in the interface between the transport system and the mass sensitive detector.

The present invention also provides a method for separation and analysis of sample components, using the integrated separation and analysis system disclosed in the present invention. The method comprises the steps of:

A) Mixing the sample components with the mobile solid phase,

B) carrying the mobile solid phase and the sample components by a transport system comprising a transport fluid, C) desorbing the sample components from the mobile solid phase, D) detaching the desorbed sample components from the solid phase, and E) analysing the sample components desorbed from the mobile solid phase with a mass sensitive detector.

Use of the described integrated system according to the invention yields a decrease in sample component losses during separation and analysis of one or more samples, as well as an ability to analyze smaller sample volumes. The invention thus saves sample, time and money. Furthermore, ageing of the solid phase in the separation system is circumvented since a new mobile solid phase is used in every new sample component separation and analysis.

SHORT DESCRIPTION OF DRAWINGS

FIG. 1 shows a schematic view of a separation utilizing a mobile solid phase in a partial filling application[17,18] of CEC.

[17]L. Vaitcheva, J. Mohammad, G. Pettersson, S. Hjertén *J. Chromatogr.* 1993, 638, 263–267.
[18]A. Amini, U. Paulsen-Sorman, D. Westerlund, *Chromatographia* 1999, 36, 35.

FIG. 2 shows a charged residual model (CRM). CRM is the fast size reduction of a small (nanometer to micrometer) charged droplet accelerated in an electric field.

FIG. 3 shows a schematic view of an integrated separation and analysis system for analysis and separation of at least one sample component. The integrated system comprises a mass-sensitive detector (1) with an ionization source (2), at least one mobile solid phase (3), at least on e sample component (4), a transport system in which the sample components and the mobile solid phase is transported (5), and at least one transport fluid (6). The sample components are separated in the interface between the transport system and the mass sensitive detector.

FIG. 4 shows plastic particles with diameters of 300–800 nm manufactured with imprints of the beta-blocker (S)-propranolol, Sigma (St. Louis, Mo., USA) through polymerization of 108,7 mM methacrylic acid (MAA), Merck (Hohenbrunn, Germany), 108,7 mM trimethylolpropane trimethacrylate (TRIM) Aldrich (Gillingham, UK), 2,44 mM azobisisobutyronitrile (AIBN) Sigma (St. Louis, Mo., USA), 13,6 mM (S)-propranolol and 3,824 mL acetonitrile (AcN)[12].

[12]Schweitz, L., Spégel P., Nilsson, S. *Analyst* 2000, 125, 1899–1901.

Figure 7:
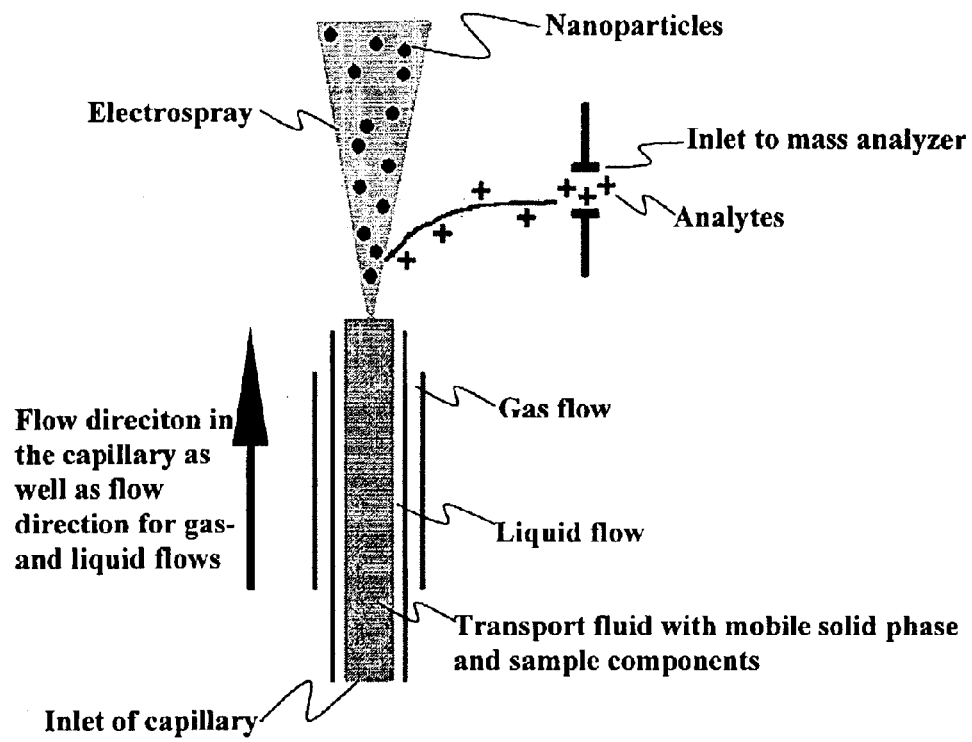

FIG. 7 shows schematically how the capillary, comprising transport fluid, mobile solid phase and sample, is coupled to a mass spectrometer with an orthogonal ionization source. A gas flow (neubilizer gas) and a liquid flow (sheath liquid) are connected to the out-let of the capillary to facilitate mobile solid phase and transport fluid to be sprayed straight out of the capillary, while the analytes deviate from the electro spray and pass into the mass analyzer.

Figure 8:
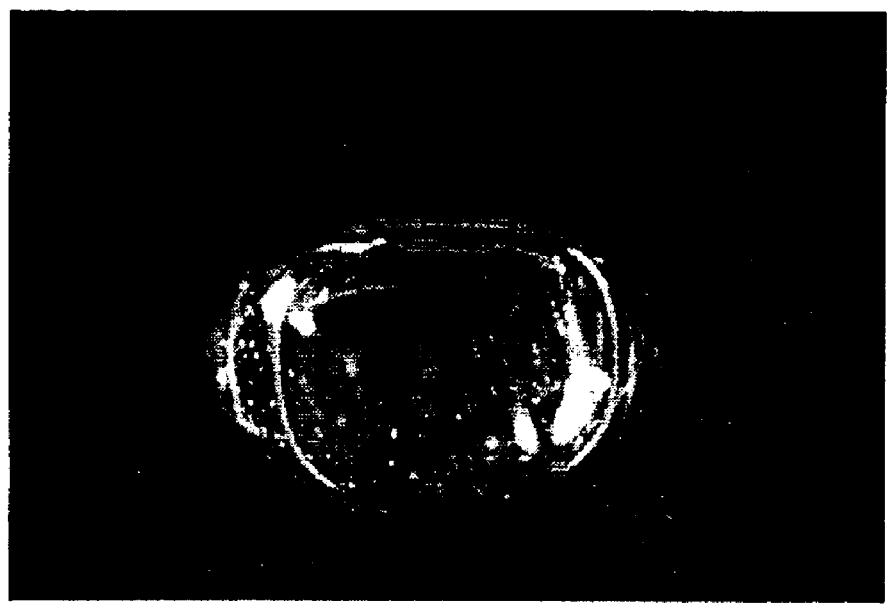

FIG. 8 shows a levitated droplet containing solid phase particles.

Figure 9:
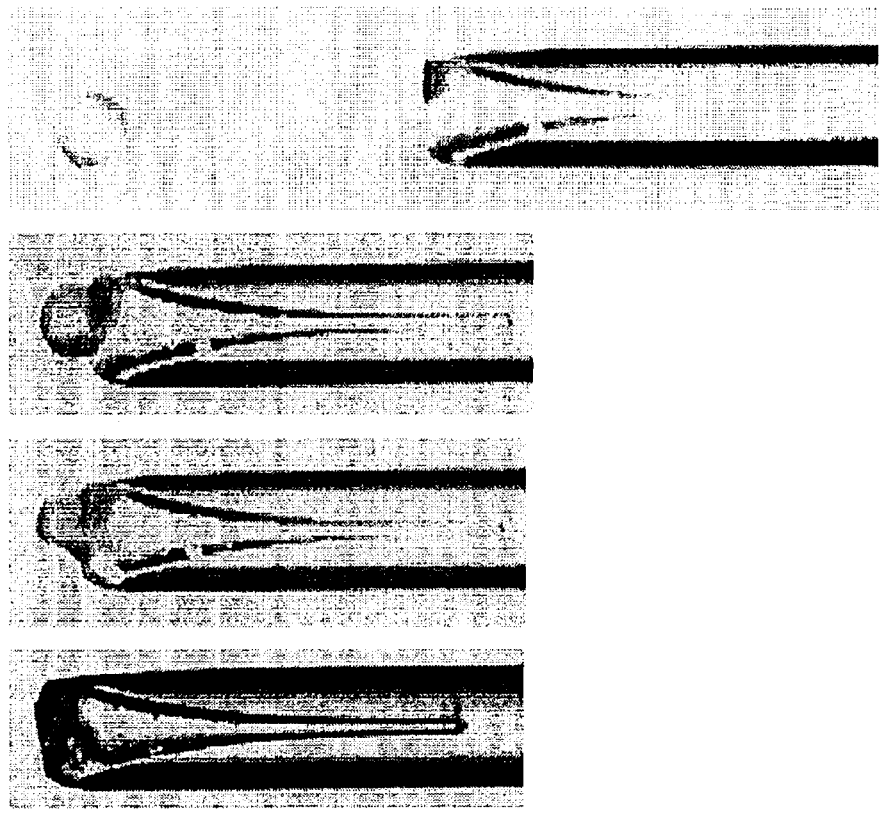

FIG. 9 shows a series of pictures from an injection.

Figure 10:
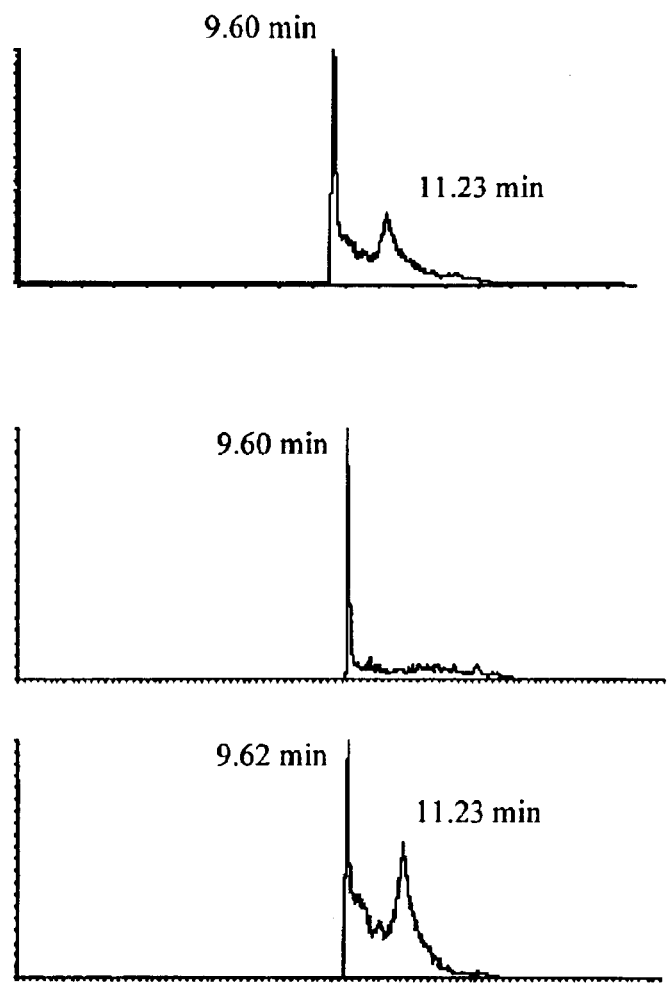

FIG. 10 shows the chromatogram from analysis of molecular weight of the sample molecules. The chromatogram from the analysis can be seen in FIG. 10 (top). The middle of FIG. 10 shows detection of cAMP only while the bottom of FIG. 10 only shows propranolol. cAMP (molecular weight 330 g/mol) eluted after 9.6 minutes, while propranolol was eluted after 11.2 minutes.

Figure 11:
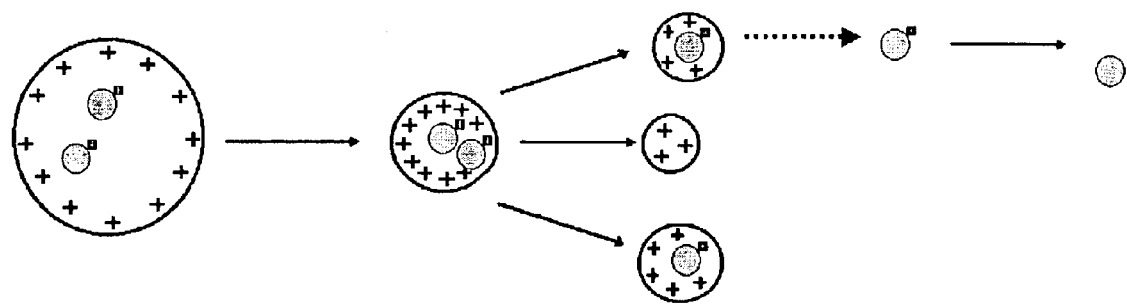

FIG. 11 shows a schematic view of CRM for droplets with solid phase particles. The grey circles in FIG. 11 illustrate solid phase particles, '+' illustrates ions in the solvent and black squares on the grey circles illustrate sample components (propranolol). The dashed line in the figure illustrate several cycles of evaporation and droplet explosion.

Figure 12:
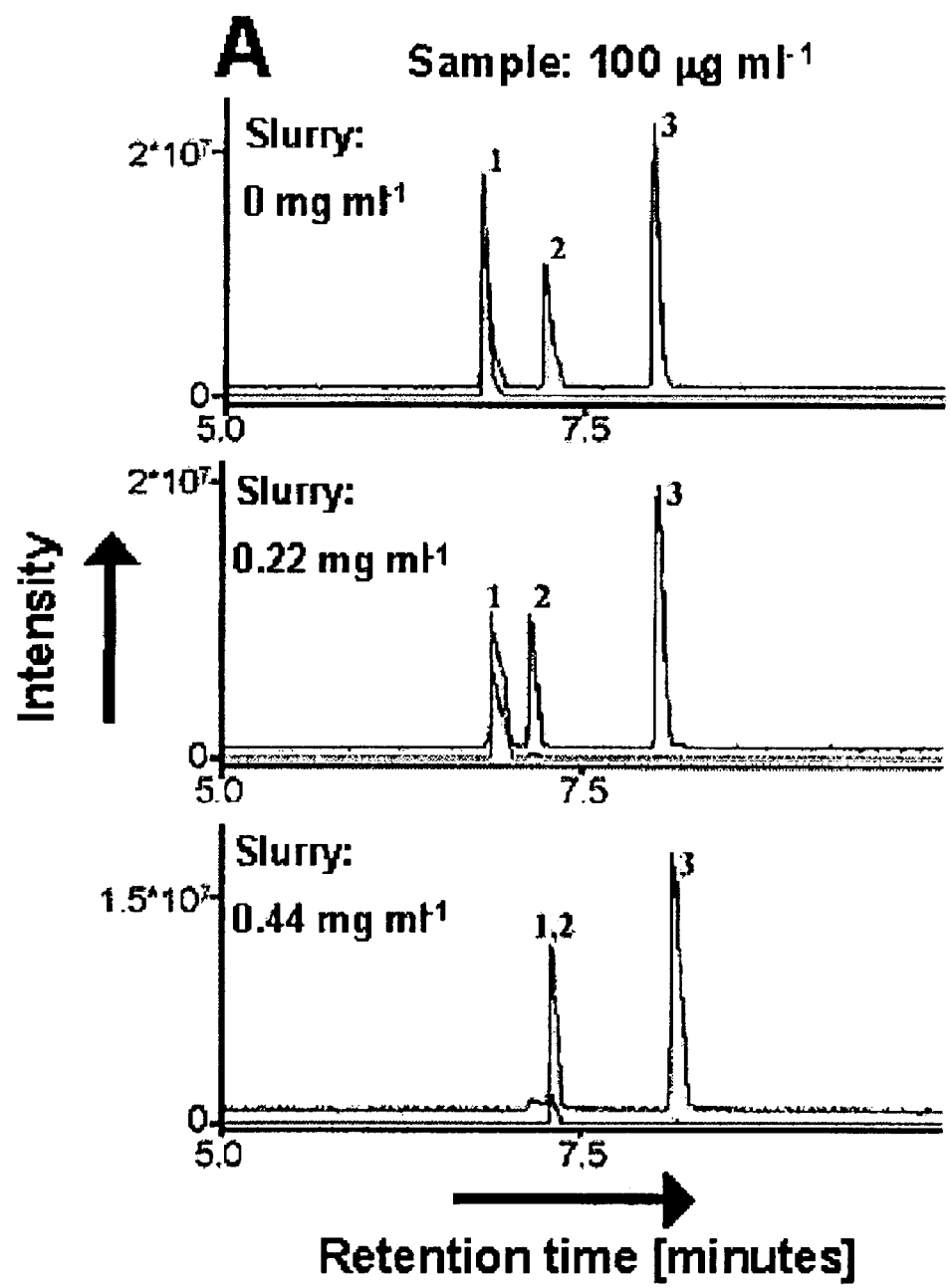

FIG. 12 shows an electrochromatogram from separations of nortriptyline (peak A), salbutamol (peak B) and diphenhydramine (peak C) (the elution order is determined by reconstructed ion chromatograms (RIC), not shown) at different slurry concentrations (0.11, 0.22 and 0.44 mg mL$^{-1}$; top to bottom). Each chromatogram shows the total ion chromatogram.

DETAILED DESCRIPTION OF THE INVENTION

Definitions

The term "integrated separation and analysis system" is herein intended to mean a separation system and an analysis system, in which several components are efficiently connected, thus enabling the integrated system in a single process.

The term "mass sensitive detector" refers to an apparatus that is analyzing or separating ions or molecules concerning mass or charge or combinations thereof.

The term "mass analyzer" referes to an apparatous that analyzes or separates ions or molecules concerning mass and/or charge. The mass anayzer is thus part of the mass sensitive detector.

The term "ionization source" refers an apparatus that allows ions to be formed from molecules or ions.

The term "angled ionization source" refers to an ionization source that is in a measurable angle, determined from the outlet of the transport system to the inlet of the mass analyzer.

The term "detector" refers the detector present in the mass sensitive detector. The detector registers or detects ions or molecules.

The term "solid phase" refers to a particle based material that is solid.

The term "mobile solid phase" describes that the solid phase is mobile, i.e. it moves in a transport fluid or it is carried by a transport fluid.

The term "particle based material" refers to crystalline, amorphous or solid bodies interconnected by covalent bonds or very strong non-covalent bonds.

The term "very strong non-covalent bonds" refers bonds that connects a non-covalently bound assembly of molecules disabling this assembly to be dissolved in the transport fluid.

The term "transport fluid" refers to a fluid or super critical fluid that travels through the transport system. The sample, containing the sample components, and the mobile solid phase can be transported and/or migrate in the transport fluid through the transport system.

The term "transport system" refers to the equipment or apparatus that is used to transport the transport fluid and/or the mobile solid phase, as well as the sample components to, by or into the mass sensitive detector.

The term "selector" refers to the unit that has selectivity for one or more of the sample components.

The term "online" refers to a course of events in the transport system.

The term "offline" refers to a course of events that is outside the transport system.

The term "qualitative separation and/or analysis" refers to separations and or analyses conducted in order to identify one or more of the sample components in the sample according to their characteristics.

An Integrated Analysis and Separation System

Figure 3:
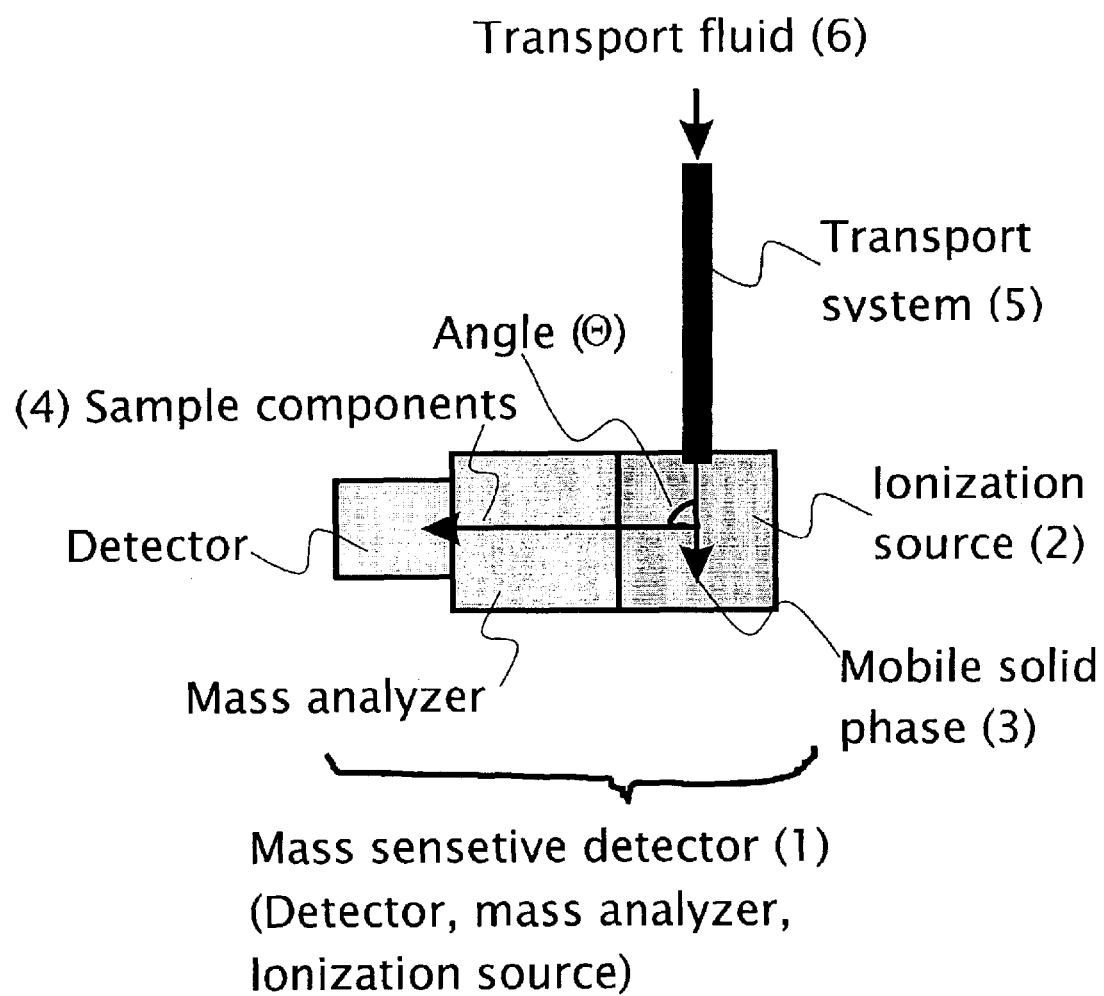

The present invention provides an integrated separation and analysis system for analysis and separation of at least one sample component. The invention comprises a mass-sensitive detector (1) with an ionization source (2), at least one mobile solid phase (3), at least on e sample component (4), a transport system in which the sample components and the mobile solid phase is transported (5), and at least one transport fluid (6). The sample components are separated in the interface between the transport system and the mass sensitive detector (FIG. 3).

In one embodiment of the invention the mobile solid phase has affinity for the sample components.

In another embodiment of the system the sample components are desorbed from the mobile solid phase and separated from the mobile solid phase prior to the entrance of the sample components into the mass sensitive detector.

In another embodiment of the system the ionization source comprises an electro spray ionization unit in which the sample components are separated from the mobile solid phase.

In another embodiment of the system the ionization source is angled.

In another embodiment of the system the ionization source is an orthogonal electro spray ionization source.

In another embodiment of the system the sample components are desorbed from the mobile solid phase inside the transport system.

In another embodiment of the system the sample components are desorbed after the transport system, but prior to the mass sensitive detector.

In another embodiment of the system the mobile solid phase is chosen on basis of characteristics being that it shows lower total interaction forces to the sample components than the forces accelerating the sample components towards and into the mass analyzer.

In another embodiment of the system the mobile solid phase may be characterized as having properties selected from the group consisting of positively charged, negatively charged, zwitter ionic, ampholytic, neutral, hydrophobic, hydrophilic, mono disperse, poly disperse and mixtures thereof.

In another embodiment of the system the mobile solid phase is selected from the group consisting of solid particles, porous particles, hollow particles and mixtures thereof.

In another embodiment of the system the sample components are positively charged and the mobile solid phase is negatively charged.

In another embodiment of the system the sample components are negatively charged and the mobile solid phase is positively charged.

In another embodiment of the system the sample components are charged, negatively and/or positively, and the mobile solid phase is neutral.

In another embodiment of the system the sample components are neutral and the mobile solid phase is charged positively and/or negatively.

In another embodiment of the system the mobile solid phase is selected from the group consisting of crystalline material, cross-linked polymer, linear polymer, derivatized silica, underivatized silica, cross-linked micelles, cells, such as mammalian cells, liposomal structures, bacteria, viruses, cell organelles and mixtures thereof.

In another embodiment of the system the mobile solid phase is modified by one or several selectors selected from the group consisting of cyclodextrines, crown ethers, antibodies, macromolecules, dendrimers and mixtures thereof.

In another embodiment of the system the mobile solid phase is composed of 1–10 mobile solid phases, such as 1, 2, 3, 4, 5, 6, 7, 8, 9, or 10 solid phases. Also, more than 10 solid phases may be used in the system, such as 20, 30, 50, or 100 solid phases.

In another embodiment of the system the transport fluid is selected from the group consisting of super critical fluid, liquid, gas, and mixtures thereof.

In another embodiment of the system the sample components are selected from the group consisting of organic compounds, inorganic compounds, metal inorganic compounds, proteins, such as enzymes, hormones, cytokines; peptides, such as oligopeptides and polypeptides; amino acids, nucleic acids, such as DNA or RNA; nucleotides, carbohydrates, lipids, glyco proteins, prions, macromolecules, cell organelles, such as mitochondria, cell nuclei, ribosome's, cell membranes, viruses, bacteria, pharmaceutical substances and mixtures thereof.

In another embodiment of the system the transport fluid, the sample components and the mobile solid phase are forced to flow using a driving force selected from the group consisting of hydrodynamic flow, mechanic flow, electroosmotic flow, and mixtures thereof.

In another embodiment of the system the transport system is selected from the group consising of chromatographic systems, electrophoretic systems, systems based on centrifugal forces, and mixtures thereof.

A Method for Separation and Analysis of Sample Components

The invention also provides a method for separation and analysis of sample components using the integrated separation and analysis system according to the invention. The method comprises the steps of a) mixing the sample components with the mobile solid phase b) carrying said solid phase and the sample components by a transport system containing a transport fluid, c) desorbing the sample components from the mobile solid phase, d) analysing sample components desorbed and separated from the solid phase using a mass sensitive detector.

In one embodiment of the method the sample components are interacting with the mobile solid phase.

In another embodiment of the method the sample components are desorbed from the solid phase and separated from the mobile phase prior to the entrance into the mass sensitive detector.

In another embodiment of the method the sample components are desorbed from the solid phase inside the transport system.

In another embodiment of the method the sample components are desorbed from the solid phase after the transport system but prior to the mass sensitive detector.

In another embodiment of the method the sample components and the mobile solid phase in a) above are mixed continuously online.

In another embodiment of the method the sample components and the mobile solid phase in a) above are mixed offline.

In another embodiment of the method the sample components in e) above are analyzed qualitatively and or quantitatively.

Use of the System

The invention also discloses the use of the integrated system according to the invention, for separation and analysis of at least one sample component qualitatively and or quantitatively. The separations and analyses may be enantiomer separations, diasteromer separations, isomer separations, determination of break down patterns of pharmaceuticals, determination of pharmaceuticals in body fluids as well as determination of toxic compounds in organisms, humans and animals.

Description of the System

The invention, accordingly, concerns an integrated separation and analysis system comprising a transport system, a transport fluid, a mass sensitive detector, a mobile solid phase as well as a sample comprising one or more sample components.

The mass sensitive detector is an instrument, e.g. a mass spectrometer, which is able to detect molecules or ions according to their mass and/or their charge. The mass sensitive detector may, according to the invention, comprise (FIG. 3) among other components an ionization source, a mass analyzer, and a detector. The mass sensitive detector may not have to comprise all of these parts, i.e. the ionization source, the mass analyzer, and the detector.

The ionization source may be EI (electron impact), ES (electro spray) or ESI (electro spray ionization) and nano spray, MALDI (matrix assisted laser desorption ionization), CI (chemical ionization), FAB (fast atom bombardment), APPI (atmospheric pressure photo ionization), APCI (atmospheric pressure chemical ionization), or another apparatus in which ions may be formed out of molecules or ions. The ionization source may be an angled ionization source.

The angled ionization source may be an ionization source with a normal from the outlet of the transport system in an angle θ (0<θ<360) from the inlet to the mass analyzer, e.g. an orthogonal ESI with the inlet to the mass analyzer angled 90° (FIG. 3). An angled ionization source may for instance be of those types that are used in the Waters ZQ mass detector or in the Agilent Technologies LC/MSD ion trap SL mass spectrometer with ESI.

The mass analyzer may be a TOF (time of flight), a quadropol or quadropoles, ion trap, magnetic sector, FTICR (Fourier-transform ion cyclotron resonance) or any other apparatus that do analyze or separate ions or molecules according to their size and/or charge.

The detector registers or detects ions or molecules (one, several or all). The mechanism behind detection or registration may be based on the principle that the ions are brought into physical contact with devices that registers the contact and eventually enhance it and transforms it into a current, such as CTEM (channeltron electron multiplier) or a CPEM (channelplate electron multiplier). Detection or registration may also be based on the FTICR (Fourier-transform ion cyclotron resonance) principle.

The solid phase is a particle based material that is solid in contrast to the transport fluid that is a fluid or a supercritical fluid.

The mobile solid phase is an interaction phase similar to the stationary phase that is used in LC, but with the important difference that the mobile solid phase is mobile, i.e. it is carried by and/or moving in the transport fluid.

The particle that are used as mobile solid phase are solid bodies that may consist of amorphous or crystalline materials interconnected by covalent bonds or very strong non-covalent bonds, e.g. polymers, silica, minerals, metals or polymer granules. These particles may be spherical or of any more or less irregular or regular shape. The particle is a solid body with a size in-between 5 nanometer and 10 micrometer. Cross-linked polymer particles made of e.g. methacrylates, acrylates, styrenes, acryl amides and vinyl pyridines may be used as solid phase. Silica derivatized with e.g. C18, C8, C4 as well as hydrocarbon chains of other length, amino silanes, epoxy silanes, alcohols, carboxylic acids, cyano groups, sulphonates, polyethylene imines, poly vinyl alcohols as well as underivatized silica may be used as solid phase. Cross-linked micelles, cells, e.g. all types of human cells, cells from mammalians, birds, fishes and plants may be used as solid phase. The cells may be blood cells or tissue cells. Viruses, e.g. HIV, bacteria, e.g. e-coli, cell organelles, e.g. mitochondria, cell membranes, cell nuclei and ribosome's may also be used as solid phase. The solid phase may also be a molecularly imprinted polymer and solid phases with immobilized selectors. The immobilized selectors may be e.g. cyclodextrines, antibodies, dendrimers, and synthetic selectors, macromolecules, such as proteins, DNA, RNA, glycol proteins, cellulose and cellulose derivatives.

The sample, containing the sample components, and the mobile solid phase may be carried with or move in the transport fluid.

The transport system is the equipment that is used in order to introduce the transport fluid and/or the mobile solid phase and/or the sample containing sample components to the mass sensitive detector.

The transport system contains a flow and a flow column.

The flow is the flow of transport fluid through the flow column. The flow may be:

(A) Hydrodynamically pumped flows, e.g. from a pump, from a syringe, using gravity, using pressure, using rotation, using vacuum as well as all present and future transport systems that are based on hydrodynamic flows. GC and LC systems as well as CD systems (centrifugal forces) are based on hydrodynamic flows.

(B) Electronkinetically driven flows, e.g. electrophoresis systems.

(C) Mechanical transport systems based on e.g. acoustics, optics, magnetism and/or shearing forces.

The flow may also be a combination of the flow types in (A) and/or (B) and/or (C). An example of a combination is pressurized capillary electrochromatography (a combination of (A) and (B)).

The magnitude of the flow may range from $1*10^{-23}$ liter per minute up to a liter per minute. The flow may be laminar or turbulent. The magnitude of the flow may be decreased by splitting or increased using make-up flows.

The flow is directed towards the mass sensitive detector through a flow column that may be:

(A) A column, e.g. a LC column with a cross section in-between 1 and 100 millimeter.

(B) A capillary. The capillary may be constructed out of quarts, fused silica, glass, metal, plastic polymer or polymer or a combination of the different materials (e.g. a fused silica capillary covered with the polymer poly imide). The capillary may be a GC-capillary, a LC-capillary, a CE-capillary or a capillary suited for electrochromatography. Typical diameters for the capillaries range from 0.5 micrometers up to 1000 micrometers. The outlet of the capillary may be sharpened or drawn into a sharp tip, e.g. nano spray capillaries or nano spray tips, and covered with metal, graphite, or polymer.

(C) A chip. The chip may be constructed from quartz, glass, polymers, plastic polymers, liquid crystals or metals. Typical inner diameters for the chip flow column range from 0.5 micrometers up to 2000 micrometers.

The flow column may be a combination of (A) and/or (B) and/or (C). For instance, a chip with a nano spray tip is a combination of (B) and (C), and a HPLC column that ends in a capillary or a nano spray tip is a combination of (A) and (B).

The sample may contain one or several sample components. The sample components may be selected from the group consisting of organic components, inorganic components, metal organic components, amino acids, peptides, nucleotides, carbohydrates, polymers, fatty acids, lipids, pharmaceutical substances, macromolecules, as well as derivatives of these, cells, organelles, viruses, bacteria, or mixtures thereof. A derivative is for instance a chemically or enzymatically modified substance or compound.

The following section describes the invention more into detail and is by no means intended to restrict the scope of the invention.

Embodiments of the System

The present invention describes an integrated separation and analysis system for separation and analysis of in samples present sample components. Characteristic for this invention is that it contains a mass sensitive detector, a solid phase that is able to interact with one or more of the sample components present in the sample and a transport system for the mobile solid phase, the sample components and the transport fluid. The invention further discloses the in the separation system present mobile solid phase and one or more of the sample components for the mass sensitive detector. The invention is based on the desorption of one or more sample components that are present on or in the mobile solid phase prior to the entrance into the mass analyzer and the exclusion of the mobile solid phase from the mass analyzer in the same event.

The invention here described possesses several benefits over existing methods and techniques:

1. The invention enables a direct and close contact between the solid phase, which is present in the separation system, and the analysis system. This simplifies the handling of very small sample volumes and sample amounts as well as analysis of sample components with one and only one mobile solid phase particle is enabled.
2. The close contact that is created between the solid phase and the mass analyzer enables sample components, which are present inside the solid phase, to be analyzed. Sample losses due to adsorption to the solid phase are thus minimized.
3. Every new sample separated and analyzed will meet an entirely new solid phase. Irreversible adsorptions to the solid phase, which eventually will cause irreversible alterations in the separation system and column ageing, are no longer a concern. The repeatability and reproducibility of the invention is thus excellent.
4. Extraction of sample components may be performed outside the system where after analysis of all in the extraction system present substances is performed without the need for washing and elution.

The invention may easily be automated and it is also compatible with airborne systems[19], which further strengthens stated advantages in 4) above.

[19]Santesson, S.; Andersson, M.; Degerman, E.; Johansson, T.; Nilsson, J.; Nilsson, S. *Anal. Chem.* 2000, 72, 3412–3418.

The transport system may be based on all present and in the future possible transport systems for transport fluids in which a mobile solid phase may be transported. A capillary electrochromatographic system with the mobile solid phase introduced continuously into the electrolyte or as a plug, as in partial filling applications, may be used. The space in which the mobile solid phase is carried or migrates in may be a capillary, a rectangular channel or of any other geometry. The transport system may also be chip based, e.g. silica chips or plastic chips.

The sample, including sample components, is incubated with the mobile solid phase prior to the entrance of the sample components in the mass analyzer. The incubation may be performed off-line, e.g. in a wall-less levitated sample handling system or on-line during electrophoretic migration and/or electroosmotic pumping along or into the transport system.

The analytical system may by itself, or in combination with the separation system or by suitable choice of mass sensitive detector, transport system, mobile solid phase, transport fluid and sample discriminate the entrance of the mobile solid phase into the mass analyzer while the sample components are desorbed from the mobile solid phase allowing them to enter the mass analyzer. This may be achieved by choosing a suitable ionization source in the mass sensitive detector, which may be an angled ionization source, e.g. an orthogonal ESI ionization source. The preference for the sample components compared to the mobile solid phase may be based on differences in charge to size ratio between the sample components and the mobile solid phase.

The described invention is based on, in the case when electro spray ionization is used, the fact that interactions between sample component or sample components and mobile solid phase are weaker than the force that transports the sample component or the sample components towards the mass analyzer. In chromatography, only a few sample components will be bound to the solid phase while the others are free in the transport fluid. Some sample components interact only negligible or not at all with the solid phase. The invention concerns analysis of sample components bound to the solid phase and sample components free in the transport fluid.

While the mobile solid phase, sample components and the transport fluid are leaving the transport system, a spray of positively or negatively charged droplets is formed. Evaporation from the droplet makes the droplet reach the Rayleigh limit and explode. After several cycles, all the solvent is evaporated and the positive charges, alternatively the negative charges have been transferred to the sample components and the mobile solid phase. The sample component or the sample components receive one or more positive charges, or negative charges, depending on structure or functionality and if the electrospray is performed in positive or negative mode.

A charged sample component in an electrical field is subjected to a force according to equation (1):

$$F = zeE \quad (1)$$

F=Accelerating force on a charged sample component in an electrical field.
z=Charge of sample component
e=Charge of an electron ($1.60*10^{-19}$ C)
E=Electrical field strength
The force, for a sample component with one charge in an 8 kV field, will be:

$$F = 1*1.60*10^{-19}*8*10^3 N = 1.28*10^{-15} N.$$

The interaction force between the sample component and the mobile solid phase can roughly be estimated from equation (2):

$$F = \Sigma(C/r^6) \quad (2)$$

F=Force between sample components and the mobile solid phase.
C=Coefficient dependent on the types of interactions.
r=Distance between sample components and the mobile solid phase.

Equation (2) has a limited validity and do not include higher interactions such as multi-pole interactions. Also, the sample components and the mobile solid phase are assumed to have free mobility in relation to each other.

The presence of a hydrophobic effect can be neglected if a complete solvent evaporation takes place. The strongest forces that then can be present are polar interactions and possibly direct attraction between oppositely charged sample components and mobile phase. If the sample component and the mobile solid phase are chosen so that they will not have opposite charges, this force will not occur. The other forces, according to equation (2) have very limited reach. Repulsive forces occur at short distances, which can be assumed by the hard sphere approximation. A small displacement amongst the sample components and the mobile solid phases will move the sample component into an area where the force towards the mass analyzer will dominate, or towards the strong repulsive area which is approximated by the hard sphere assumption. Also within the optimal interaction distance, the force towards the mass analyzer will for most cases be far greater than the interaction force.

EXAMPLE

Below are examples of how the invention may be used.

Example 1

One disadvantage of today's separation systems is that a stationary phase has been immobilized inside a column or a capillary, after which it is employed during a long time for a large number of different, or similar, separation applications. The quality of the column will continually change, and the column has to be changed after a certain time. The changes of the column will lead to poor reproducibility during the time it is employed.

Figure 1:
Figure 1:
Figure 1:
Figure 2:
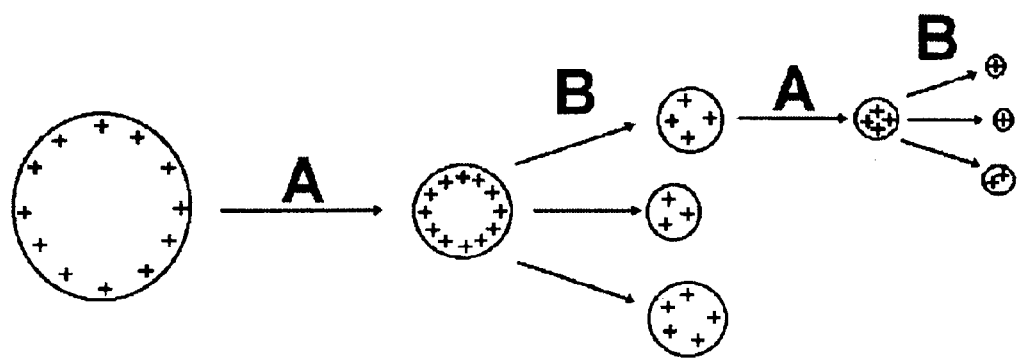

One way to circumvent these problems is to use a mobile solid phase, or a pseudo stationary phase, in a partial filling application of CE (FIG. 1). With this technique, a new solid phase will be employed for each separation. One needs to make sure that the sample components reach the detection window prior to the mobile solid phase. If this is not successfully achieved, the presence of the mobile solid phase during elution of the separated sample components will affect (negatively) the detection. Fluorescence detection would minimize the problem, but this technique only works for analytes which posses fluorescence. UV-VIS detection may be impossible, as well as analysis with a traditional mass spectrometer.

Figure 4:
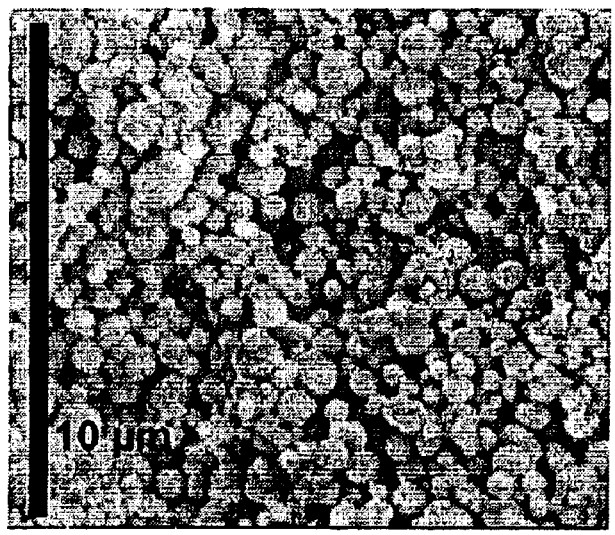
Figure 5:
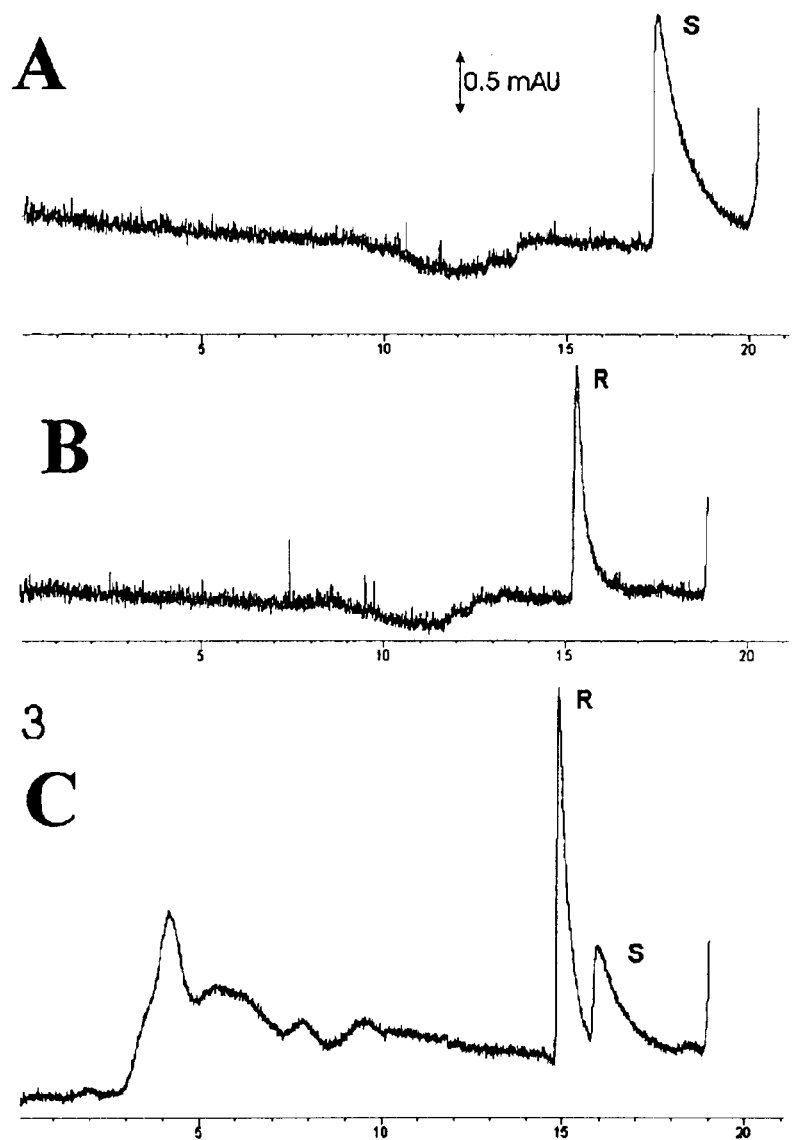
FIG. 5 shows the analysis of obtained particles in capillary electrochromatography, HP$^{3D}$CE Hewlett Packard (Waldbronn, Germany) utilizing the partial filling technique.

Plastic particles with diameters of 300–800 nm (FIG. 4) were manufactured with imprints of the beta-blocker (S)-propranolol, Sigma (St. Louis, Mo., USA) through polymerization of 108,7 mM methacrylic acid (MAA), Merck (Hohenbrunn, Germany), 108,7 mM trimethylolpropane trimethacrylate (TRIM) Aldrich (Gillingham, UK), 2,44 mM azobisisobutyronitrile (AIBN) Sigma (St. Louis, Mo., USA), 13,6 mM (S)-propranolol and 3,824 mL acetonitrile (AcN) [12]. The solution was transferred to a borosilicate glass test tube fitted with a screw cap and degassed by ultrasonication (10 mins) and by a stream of nitrogen gas through the solution (6 min), before it was positioned under a UV-lamp inside a freezer (−26° C. over night). The particles were washed with methanol/acetic acid (9/1 v/v) and methanol by centrifugation and re-suspension in an ultrasonic bath. The obtained particles were evaluated in capillary electrochromatography, HP$^{3D}$CE Hewlett Packard (Waldbronn, Germany) utilizing the partial filling technique (FIG. 5): The electrolyte consisted of acetonitrile/25 mM phosphoric acid+triethanolamine pH 3.5 (90/10 v/v). The particles were suspended in electrolyte to a concentration of 5 mg/mL. The particle suspension was injected hydrodynamically at 50 mbar during 100 sec in a 190 cm capillary (181.5 cm effective length) with 100 micro meter inner diameter (i.d.), 375 micro meter outer diameter (o.d.) Composite Metal Services (Worcester, GB). Then followed the injection of the sample (S)-propranolol (FIG. 5A), (R)-propranolol Sigma (St. Louis, Mo., USA) (FIG. 5B) and (rac)-propranolol Sigma (St. Louis, Mo., USA) (FIG. 5C) electrokinetically at 10 kV during 10 sec. The separation voltage was 30 kV and the separation temperature was 60° C.

[12]Schweitz, L., Spégel P., Nilsson, S. *Analyst* 200, 125, 1899–1901.

Figure 6:
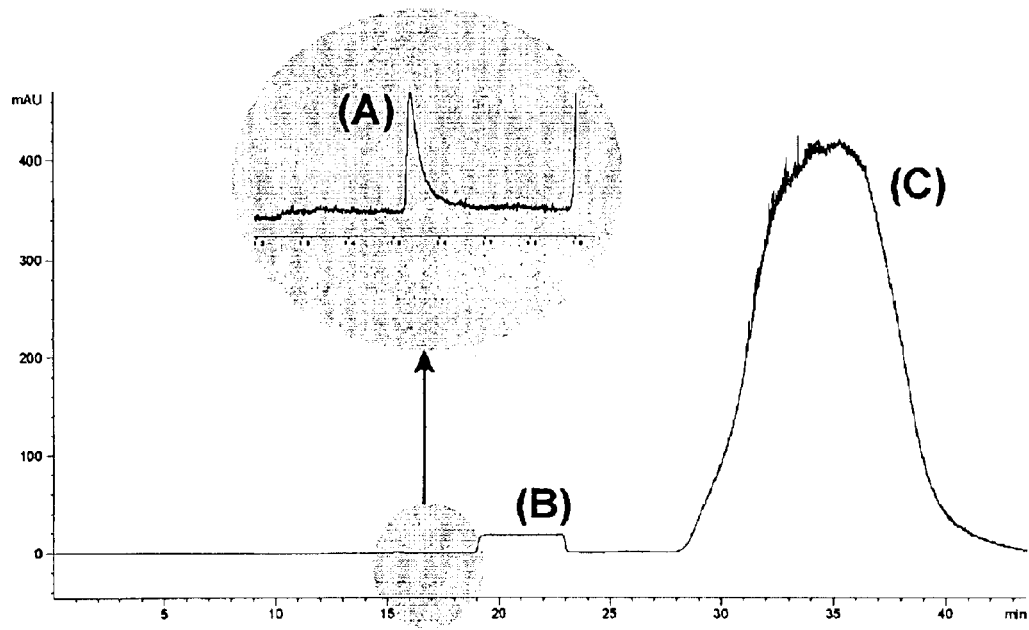
FIG. 6 shows that the sample components absorption of UV-light (A) is considerably lower than the UV-absorption by the particle slurry (B) and (C).

In the above shown application, a fairly large quantity of sample has been analyzed. More rapid separations have been achieved in capillaries with lower EOF, higher separation voltages and less amount of sample and mobile solid phase injected[12]. The technique involves problems with choosing the amount of mobile solid phase that can be injected, with respect to the migration rate of the sample components, and therefore problems to ensure that the sample components reach the detection window prior to the mobile solid phase. The mobile solid phase (plastic particles) that has been employed in this study makes detection of molecules which co-elute with the mobile solid phase impossible (FIG. 6). FIG. 6 shows that the sample components absorption of UV-light (A) is considerably lower than the UV-absorption by the particle slurry (B) and (C).

[12]Schweitz, L., Spégel P., Nilsson, S. *Analyst* 2000, 125, 1899–1901.

The above exemplified separation is valid for a system with positively charged sample components and a negatively charged mobile solid phase. If another combination of charges is employed, the procedure would be more difficult. The case with neutral ample components and negatively charged particles would only give an elution window (a time window where detection can take place) between peak B and peak C in FIG. 6. If the analyte molecules and the particles have the same charge, the analysis may be impossible or demand an unmanageable long capillary, due to co-elution of particles and sample components.

A separation system with an, for each analysis, new mobile solid phase, can be created through an orthogonal electro spray ionization source (FIGS. 3 and 7) that excludes the mobile solid phase from the mass analyzer, and thereby makes detection possible without the disadvantages mentioned above. Sample components will, due to the fact that the forces that affect them in the electrical field are greater than their interaction forces towards the particles, be accelerated into the mass analyzer. One example of a commercially available mass spectrometer with an orthogonal ionization source is the Waters ZQ mass detector.

Example 2

A development of example 1 makes a continuous separation and analysis system possible where the mobile solid phase is pumped by EOF towards and into the orthogonal electro spray ionization source. With the given band broadening of the peaks (originating from poly-clonality of the molecular imprints on the mobile solid phase) one injection can be made each minute. Each sample that is injected will be transported through a totally new mobile solid phase. A mass spectrometer with an orthogonal electro spray ionization source makes detection of the analytes possible. FIG. 3 and FIG. 7 shows schematically how the capillary (containing transport fluid, mobile solid phase and sample) is coupled to a mass spectrometer with an orthogonal ionization source. A gas flow (neubilizer gas) and a liquid flow (sheath liquid) are connected to the out-let of the capillary to facilitate mobile solid phase and transport fluid to be sprayed straight out of the capillary, while the analytes deviate from the electro spray and pass into the mass analyzer.

Example 3

Polymeric solid phase particles with average diameters between 100–300 nm were synthesized from 90 mM butyl methacrylate (BMA) Sigma (St. Louis, Mo., USA) and 90 mM trimethylpropane trimethacrylat (TRIM) Aldrich (Gillingham, UK). 2,44 mM azobisisobutyronitrile (AIBN) Sigma (St. Louis, Mo., USA) was used as initiator and 4,293 mL acetonitrile (AcN) was used as solvent for the polymerization. Otherwise the particles were synthesized according to example 1.

The solid phase particles are hydrophobic and when they are added (off-line) a water solution containing sample components, they bind sample components which are hydrophobic, while hydrophilic sample components stay in the water solution. In the experiment a levitator Dantec (Erlangen, Germany) that uses standing acoustical waves to trap liquid droplets (<1 micro-liter in volume) and to make them levitated in air[17] was used. The solid phase particles (dissolved in a water droplet) were positioned in the levitator and the sample components were injected in the levitated droplet by a flow through droplet dispenser[17]. Propranolol Sigma (St. Louis, Mo., USA) was used as hydrophobic sample component and cyclic adenosine monophosphate (cAMP) Sigma (St. Louis, Mo., USA) was used as hydrophilic sample component.

[17]L. Vaitcheva, J. Mohammad, G. Pettersson, S. Hjertén *J. Chromatogr.* 1993, 638, 263–267.

Mixing in the levitated droplet was achieved by adjusting the settings on the levitator. FIG. 8 illustrates a levitated droplet containing solid phase particles. The levitated droplet was allowed to evaporate in order to increase its volume and facilitate injection into a capillary by capillary force. FIG. 9 illustrates a series of pictures from an injection. A funnel was etched by hydro fluoric acid at the end of the capillary to further facilitate the injection.

A polymeric frit (an immobilized filter) was manufactured 10 mm into the capillary to make sure that the particles did not reach the mass spectrometer[20]. The subsequent experiment was performed to show that propranolol had bound to the solid phase, while cAMP remained in the water solution. The injection end of the capillary was positioned in a vial with water/AcN (8/2 v/v) and an over-pressure of 350 kPa of nitrogen gas was applied to create a flow through the capillary. cAMP, which was dissolved in the water phase in the injection end of the capillary, was first eluted through the capillary, followed by propranolol which desorbed from the polymeric solid phase particles by the water/AcN-solution. The out-let of the capillary was positioned in the ionization source of an electro spray ionization mass spectrometer, so molecules that passed through the capillary were detected by the mass spectrometer, and their molecular weight were determined. The chromatogram from the analysis can be seen in FIG. 10 (top), the middle of FIG. 10 shows detection of cAMP only while the bottom of FIG. 10 only shows propranolol. cAMP (molecular weight 330 g/mol) eluted after 9.6 minutes, while propranolol was eluted after 11.2 minutes. The fact that propranolol was eluted later than cAMP shows that propranolol was retained by the solid phase particles, and eluted first when the water/AcN-solution was pumped through the solid phase particles. FIG. 10 (bottom) shows that propranolol partly eluted at the same time as cAMP, which is the result of over-loading of the solid phase particles, i.e. a too high concentration of propranolol was present in the levitated droplet to enable complete extraction/adsorption to the solid phase particles.

[20]Chen, J.-R.; Dulay, M. T.; Zare, R. N., Svec, F.; Peters, E., *Anal. Chem.* 2000, 72, 1224–1227.

The experiment showed that solid phase extraction of propranolol from a water solution is possible. The electro spray interface that was used in the experiment is not tolerant towards particles. Particles that are allowed to pass the capillary will enter the mass spectrometer and cause contamination and lowered sensitivity will be one consequence. It has been reported that frits have band broadening effects in capillaries, something that reduces the capillary separation systems ability to separate sample components[21]. Adsorption of particles to frits may, if the frits pores are of the same or similar sizes as the particles, cause clogging and hence block the flow through of the capillary. A capillary with a frit may therefore only be used once. The method allows a mass spectrometer which do not have an orthogonal interface (or at other angels), to be used.

[21]Behnke, B.; Johansson, J.; Bayer, E.; Nilsson, S. *Electrophoresis*, 2000, 21, 3102–3108.

Example 4

Polymer solid phase particles were manufactured and used in solid phase extraction of propranolol from a water solution containing propranolol and cAMP in a levitated droplet according to example 3. The levitated droplet was injected into a capillary and pumped through the capillary as described in example 3. The capillary in this example does not have a frit, so sample components and polymer particles reach the electro spray ionization source. The electro spray ionization source in the example is an orthogonal electro spray ionization source, where gas and liquid flows on the outside of the capillary (FIG. 7) make the particles pass straight out of the transport system, while charged sample components deviates and are accelerated into the mass spectrometer.

The mobile phase, the polymer particles, propranolol and cAMP will leave the capillary as charged droplets. The droplets undergo CRM according to the theory described previously. FIG. 11 describes CRM for droplets with solid phase particles. The grey circles in FIG. 11 illustrate solid phase particles, '+' illustrates ions in the solvent and black squares on the grey circles illustrate sample components (propranolol). The dashed line in the figure may illustrate several cycles of evaporation and droplet explosion. CRM for charged, polymer solid phase particle containing droplets with adsorbed propranolol will be terminated when no more solvent remain around the particle. The same extraction as is described in example 3 is achieved. The lack of a frit in example 4 reduces unwanted adsorption of sample components and as a consequence the band broadening is reduced. A capillary without frit may be used in several analyses.

Example 5

For complicated separation problems, where large groups of analytes of different nature should be separated, a combination of solid phases possessing different selectivity may be used. As an example, solid phases may be combined from hydrophobic particles, ionic particles and porous particles, to separate different analytes on a basis of hydrophobicity, charge and size in a single analysis. The different solid phase particle types may be introduced each separately (after each other) or all mixed together, to create and tailor-make separation systems where, normally, several subsequent separation columns are needed. The solid phase is transported by the transport fluid electrophoretically or hydrodynamically pumped towards the mass spectrometer, and is hindered from entering the mass analyzer in the orthogonal electro spray ionization source. The benefit with the described system based on an orthogonal electro spray ionization source and a mobile solid phase, is that the solid phase easily can be tailor made for each separation problem without the need to prepare, buy, get hold of or install packed columns. Also, expensive and complicated column-coupling systems are avoided. For each single new separation, a new (previously unused) solid phase is used, hence problems associated with adsorption of sample to the solid phase and aging of the solid phase are avoided.

Example 6

Experiments have been performed at a constant flow of mobile solid phase through a capillary in a capillary electrophoresis system coupled to a mass spectrometer with an orthogonal interface, for separation of 3 amines.

Synthesis of Mobile Solid Phase Particles:

Particles were synthesized according to the precipitation polymerization technique. The chemicals used in this example have the same origin as in the previous examples. A monomer containing a carboxylic acid group, methacrylic acid (MAA) 0.0545 mol $L^{-1}$, a hydrophobic monomer, methyl methacrylate (MMA) 0.0545 mol $L^{-1}$ and a cross-linking monomer, trimethylolpropane trimethacrylate (TRIM) 0.109 mol $L^{-1}$ were dissolved in acetonitrile in a borosilicate glass test tube fitted with a screw-cap. A radical initiator, 2,2'-azobis(isobutyronitrile) (AIBN), 0.0012 mol $L^{-1}$, was added the mixture and the mixture was placed in an ultrasonic bath for 10 minutes and was degassed using a flow of nitrogen gas for 6 minutes. The polymerization was initiated by UV-light and proceeded over night. The gained particles were washed by centrifugation in AcN/acetic acid (75/25 v/v) and in AcN, after which the particles were dried.

Capillary Electrochromatography (CEC) Experiment:

CEC experiments were performed using a $HP^{3D}CE$ system (Agilent Technologies, Waldbronn, Germany). A 75 cm long, 50 micrometer i.d. and 375 micrometer o.d. fused silica capillary from Polymicro Technologies (Phoenix, Ariz., USA) was used in all experiments. The transport fluid was a mix of AcN and a water buffer (1:1 v/v). The water buffer, 50 mM ammonium carbonate, was adjusted to pH=8.2 with 10% v/v ammonia/water, prior to mixing with AcN. Sample solution was prepared by dissolving nortriptyline, salbutamol and diphenehydramine in transport fluid to a concentration of 100 microgram per mL. Mobile solid phase particles were suspended in transport fluid (10, 2.5, 0.44, 0.22 and 0.11 mg $mL^{-1}$).

The capillary was filled with mobile solid phase suspended in transport fluid, after which the sample was injected in the capillary hydrodynamically (5 seconds at 50 mbar). The capillary's injection end was positioned inside a vial containing mobile solid phase suspended in transport fluid, and the separation was started (20 kV (267 V/cm)). The interaction between the analytes in the sample and the mobile solid phase particles was studied by studying changes in the retention times of the analytes at different concentrations of mobile solid phase particles in transport fluid. Due to the fact that the capillary was initially filled with mobile solid phase suspended in transport fluid, and that mobile solid phase suspended in transport fluid was infused into the capillary during the experiment, a constant flow of mobile solid phase particles was continuously flowing out of the capillary and into the ionization source.

Mass Spectrometric Detection:

Detection was performed using an Agilent Technologies LC/MSD ion trap SL mass spectrometer with ESI-ionization. The sheath liquid flow consisted of methanol, water and formic acid (1/1 v/v and 0.1% v/v) and was pumped and splitted to 6 micro liter per minute. The separation capillary was coupled to the ionization source with the aid of an Agilent Technologies triple tube coaxial nebulizer (at ground potential). The ionization source was orthogonal, i.e. the sheath liquid flow, the gas flow and the flow from the separation capillary were electro sprayed orthogonal to the inlet to the mass analyzer.

Results:

FIG. 12 shows an electrochromatogram from separations of nortriptyline (peak A), salbutamol (peak B) and diphenhydramine (peak C) (the elution order is determined by reconstructed ion chromatograms (RIC), not shown) at different slurry concentrations (0.11, 0.22 and 0.44 mg $mL^{-1}$; top to bottom). Each chromatogram shows the total ion chromatogram. A significant increase in retention time for nortriptyline and diphenhydramine can bee seen in FIG. 12, which indicates interaction between these molecules and the mobile solid phase particles. Examination of the mass spectrometer showed no signs of mobile solid phase particles entering the mass analyzer (during the total 100 hours the method was used).

What is claimed is:

1. An integrated separation and analysis system for analysis and separation of at least one sample component, comprising:
   (a) a mass sensitive detector;
   (b) an ionization source;
   (c) a sample comprising a plurality of sample components;
   (d) at least one mobile solid phase that interacts with one or more of the sample components present in the sample;
   (e) one transport system in which the mobile solid phase and the sample are transported; and
   (f) at least one transport fluid,
wherein sample components are separated from the mobile solid phase within the ionization unit of the ionization source at the interface between the transport system and the mass sensitive detector.

2. The system according to claim 1, wherein the mobile solid phase has a binding capacity for the sample component.

3. The system according to claim 1, in which the ionization source is a ionizing electro spray unit.

4. The system according to claim 3, in which the electro spray unit is an orthogonal electro spray.

5. The system according to claim 1, in which the sample component is desorbed from the mobile solid phase in the transport system.

6. The system according to claim 1, in which the mobile solid phase is chosen so that the total force between the solid phase and the sample component is weaker than the force that transports the sample component towards the mass sensitive detector.

7. The system according to claim 1, in which the mobile solid phase has a characteristic selected from the group consisting of positive charge, negative charge, zwitter-ionic, ampholytic, neutral, hydrophobic, hydrophilic, monodispers, polydispers and mixes thereof.

8. The system according to claim 1, in which the sample component is positively, charged and the mobile solid phase is negatively charged.

9. The system according to claim 1, in which the mobile solid phase is made from a material selected from the group consisting of a crystalline material, a cross-linked polymer, a linear polymer, a derivatized silica, a non-derivatized silica, a cross-linked micelle, a cell, a liposomic structure, a bacteria, a cell organelle and mixes thereof.

10. The system according to claim 9, wherein the mobile solid phase is further modified by a selector selected from the group consisting of cyclodextrines, crown-ethers, antibodies, macromolecules, dendrimers and mixtures thereof.

11. The system according to claim 1, in which the mobile solid phase comprises 1–10 mobile solid phases.

12. The system according to claim 1, in which the transport fluid is selected from the group consisting of a supercritical fluid, a gas, a liquid, and mixtures thereof.

13. The system according to claim 1, in which the sample component is selected from the group consisting of organic compounds, inorganic compounds, metal-organic compounds, proteins, such as enzymes, hormones, cytokines; peptides, such as oligopeptides and polypeptides; amino acids, nucleic acids, such as DNA or RNA; nucleotides, carbohydrates, lipids, glyco proteins, prions, macro molecules, such as cell organelles, cell membranes; viruses, bacteria, pharmaceutical substances, and mixtures thereof.

14. The system according to claim 1, in which the transport fluid, sample component and mobile solid phase is driven to flow with the aid of a force selected from the group consisting of hydrodynamic flow, mechanical flow, electrophoretic flow, and mixtures thereof.

15. The system according to claim 1, in which the transport system is selected from the group consisting of chromatographic systems, electrophoretic systems, and mixtures thereof.

16. The system according to claim 1 in which the ionization source is angled.

17. The system according to claim 1, in which the sample component is positively charged.

18. The system according to claim 1, in which the mobile solid phase is positively charged or neutral.

19. The system according to claim 1, in which the mobile solid phase is a cross-linked polymer.

20. The system according to claim 18, in which the sample component is negatively charged or neutral.

21. The system according to claim 19, in which the sample component is negatively charged neutral.

22. The system according to claim 1, in which the transport fluid is a liquid.

23. The system according to claim 21, in which the cross-linked polymer is positively charged or neutral.

24. The system according to claim 23, in which the transport fluid is a liquid.

25. The system according to claim 24, in which a driving force for the transport fluid is electroosmosis.

26. The system according to claim 25, which the transport system is an electrophoretic system.

27. A method to separate and analyze at least one sample component with the integrated separation and analysis system comprising the steps of:
  a) mixing a sample with a mobile solid phase that interacts with one or more of the sample components present in the sample;
  b) transporting the mobile solid phase and a sample with a transport system comprising a transport fluid;
  c) desorbing the sample components that interact with the mobile solid phase from the mobile solid phase;
  d) separating the desorbed sample components from the mobile solid phase; and
  e) analyzing the sample components with a mass sensitive detector.

28. The method according to claim 27, in which the sample component is interacting with the mobile solid phase.

29. The method according to claim 28, in which the sample component is desorbed and separated from the mobile solid phase before entrance into the mass sensitive detector.

30. The method according to claim 28, in which the sample component is desorbed in the transport system.

31. The method according to claim 28, in which the sample component is desorbed after the transport system, but before the mass sensitive detector.

32. The method as in one of claims 27–31, in which the sample component and the mobile solid phase are mixed online.

33. The method as in one of claims 27–31, in which the sample component and the mobile solid phase are mixed offline.

34. The method according to claim 27, in which the sample component is analyzed qualitatively or quantitatively.

* * * * *

UNITED STATES PATENT AND TRADEMARK OFFICE
CERTIFICATE OF CORRECTION

PATENT NO. : 6,909,091 B2
DATED : June 21, 2005
INVENTOR(S) : Staffan Nilsson et al.

It is certified that error appears in the above-identified patent and that said Letters Patent is hereby corrected as shown below:

Column 18,
Line 47, "a ionizing" should read -- an ionizing --.
Line 64, "positively, charged" should read -- positively charged --.

Column 19,
Line 45, "negatively charged neutral." should read -- negatively charged or neutral. --.

Column 20,
Line 7, "claim 25, which" should read -- claim 25, in which --.

Signed and Sealed this

Thirtieth Day of August, 2005

JON W. DUDAS
*Director of the United States Patent and Trademark Office*